United States Patent
Baram et al.

(10) Patent No.: US 12,385,031 B2
(45) Date of Patent: *Aug. 12, 2025

(54) SYSTEMS AND METHODS FOR GROWING A BIOFILM OF PROBIOTIC BACTERIA ON SOLID PARTICLES FOR COLONIZATION OF BACTERIA IN THE GUT

(71) Applicant: MYBIOTICS PHARMA LTD., Rehovot (IL)

(72) Inventors: David Baram, Nir-Zvi (IL); Rachel Diamant, Ein-Vered (IL); David Daboush, Mishmar David (IL)

(73) Assignee: MYBIOTICS PHARMA LTD., Rehovot (IL)

( * ) Notice: Subject to any disclaimer, the term of this patent is extended or adjusted under 35 U.S.C. 154(b) by 0 days.

This patent is subject to a terminal disclaimer.

(21) Appl. No.: 18/126,459

(22) Filed: Mar. 26, 2023

(65) Prior Publication Data

US 2023/0227806 A1    Jul. 20, 2023

Related U.S. Application Data

(63) Continuation of application No. 17/031,271, filed on Sep. 24, 2020, now Pat. No. 11,680,257, which is a
(Continued)

(51) Int. Cl.
| | |
|---|---|
| *C12N 11/02* | (2006.01) |
| *A61K 9/14* | (2006.01) |
| *A61K 35/00* | (2006.01) |
| *A61K 35/74* | (2015.01) |
| *A61K 35/741* | (2015.01) |

(Continued)

(52) U.S. Cl.
CPC ............. *C12N 11/02* (2013.01); *A61K 9/141* (2013.01); *A61K 35/74* (2013.01); *A61K 35/741* (2013.01); *A61K 35/747* (2013.01); *C12N 1/20* (2013.01); *C12N 11/04* (2013.01); *C12N 11/12* (2013.01);
(Continued)

(58) Field of Classification Search
CPC .......... C12N 11/02; C12N 1/20; C12N 11/04; C12N 11/12; C12N 11/14; A61K 9/141; A61K 35/74; A61K 35/741; A61K 35/747; A61K 2035/11; A61K 2035/115
See application file for complete search history.

(56) References Cited

U.S. PATENT DOCUMENTS 8,329,221 B2 * 12/2012 Thoorens ............. A61K 9/2054
424/489

* cited by examiner

*Primary Examiner* — Kade Ariani
(74) *Attorney, Agent, or Firm* — The Roy Gross Law Firm, LLC; Roy D. Gross

(57) ABSTRACT

The present invention provides a method, wherein the method forms a biofilm, wherein the biofilm comprises a population of at least one bacterial strain attached to particles, wherein the biofilm is configured to colonize a gut of a subject in need thereof for at least five days, when ingested by the subject, the method comprising: a. obtaining a population comprising at least one strain of bacteria; b. inoculating a growth medium containing particles with the population comprising at least one strain of bacteria; c. incubating the particles with the population comprising at least one bacterial strain for a time sufficient for the population of at least one strain of bacteria to attach to the particles; and d. culturing the population comprising at least one strain of bacteria attached to the particles in a growth medium, for a time sufficient to form a biofilm.

19 Claims, 13 Drawing Sheets

Related U.S. Application Data continuation of application No. 15/572,972, filed as application No. PCT/IB2016/000933 on May 9, 2016, now Pat. No. 10,793,847.

(60) Provisional application No. 62/159,846, filed on May 11, 2015, provisional application No. 62/159,849, filed on May 11, 2015.

(51) Int. Cl.
*A61K 35/747* (2015.01)
*C12N 1/20* (2006.01)
*C12N 11/04* (2006.01)
*C12N 11/12* (2006.01)
*C12N 11/14* (2006.01)

(52) U.S. Cl.
CPC .......... *C12N 11/14* (2013.01); *A61K 2035/11* (2013.01); *A61K 2035/115* (2013.01)

*Lactobacillus plantarum* biofilm on various matrices

Organic matrices

Pomegranate

Passion fruit

Inorganic matrices

White clay

Sand

Bentonite clay

*Lactobacillus plantarum* biofilm on various matrices
Synthetic matrices

Avicel

DCP

Solka fibers

*Acetobacter pomorum* biofilm on various matrices

Sand

Pomegranate

Organic Passion fruit

*Pseudomonas spp.* biofilm on various matrices

Organic matrices

Passion fruit

Pomegranate

SYSTEMS AND METHODS FOR GROWING A BIOFILM OF PROBIOTIC BACTERIA ON SOLID PARTICLES FOR COLONIZATION OF BACTERIA IN THE GUT

CROSS REFERENCE TO RELATED APPLICATIONS

This application is a Continuation of U.S. application Ser. No. 17/031,271 filed Sep. 24, 2020, which is a Continuation of U.S. application Ser. No. 15/572,972, filed on Nov. 9, 2017, which is a national phase of PCT Patent Application No. PCT/IB2016/000933 having International filing date of May 9, 2016, which claims the benefit of priority to U.S. Provisional Patent Application Ser. No. 62/159,846, filed on May 11, 2015, and U.S. Provisional Patent Application Ser. No. 62/159,849, filed on May 11, 2015, the entire contents of which are hereby incorporated by reference in their entirety.

FIELD OF THE INVENTION

The present invention relates to system and method for growing and encapsulating at least one strain of bacteria in a biofilm form, configured for pH dependent targeted release of the bacterial biofilm in the gastrointestinal tract.

SUMMARY

In one embodiment, the present invention provides a method,
wherein the method forms a biofilm,
wherein the biofilm comprises a population of at least one bacterial strain attached to particles,
wherein the biofilm is configured to colonize a gut of a subject in need thereof for at least five days, when ingested by the subject, the method comprising:
  a. obtaining a population comprising at least one strain of bacteria;
  b. inoculating a growth medium containing particles with the population comprising at least one strain of bacteria;
  c. incubating the particles with the population comprising at least one bacterial strain for a time sufficient for the population of at least one strain of bacteria to attach to the particles; and
  d. culturing the population comprising at least one strain of bacteria attached to the particles in a growth medium, for a time sufficient to form a biofilm.

In one embodiment, the biofilm comprising a population of at least one bacterial strain attached to particles is encapsulated with a compound configured to release the at least one bacterial strain at a pH found in the intestine of the animal.

In one embodiment, the compound configured to release the at least one bacterial strain at a pH found in the intestine of the animal is alginate.

In one embodiment, the population of at least one strain of bacteria attached to the particles is cultured in the growth medium under flow conditions.

In one embodiment, the population of at least one strain of bacteria attached to the particles is cultured in the growth medium under static conditions.

In one embodiment, the population of at least one strain of bacteria attached to the particles is first cultured in the growth medium under static conditions, followed by culture in the growth medium under flow conditions.

In one embodiment, the population of at least one strain of bacteria attached to the particles is cultured under anaerobic conditions.

In one embodiment, the population of at least one strain of bacteria attached to the particles is cultured under aerobic conditions.

In one embodiment, the particles are porous, and selected from the group consisting of: seeds, dicalcium phosphate, clay, sand and cellulose.

In one embodiment, the population comprising at least one bacterial strain is derived from gut microflora.

In one embodiment, the population comprising at least one bacterial strain is *Lactobacillus plantarum*.

In one embodiment, the population comprising at least one bacterial strain is *Acetobacter pomorum*.

In one embodiment, the biofilm formed by the method is configured for pH dependent targeted release of the bacterial biofilm in the gastrointestinal tract.

In one embodiment, the biofilm comprises two or more strains of bacteria.

DETAILED DESCRIPTION

Figure 1:
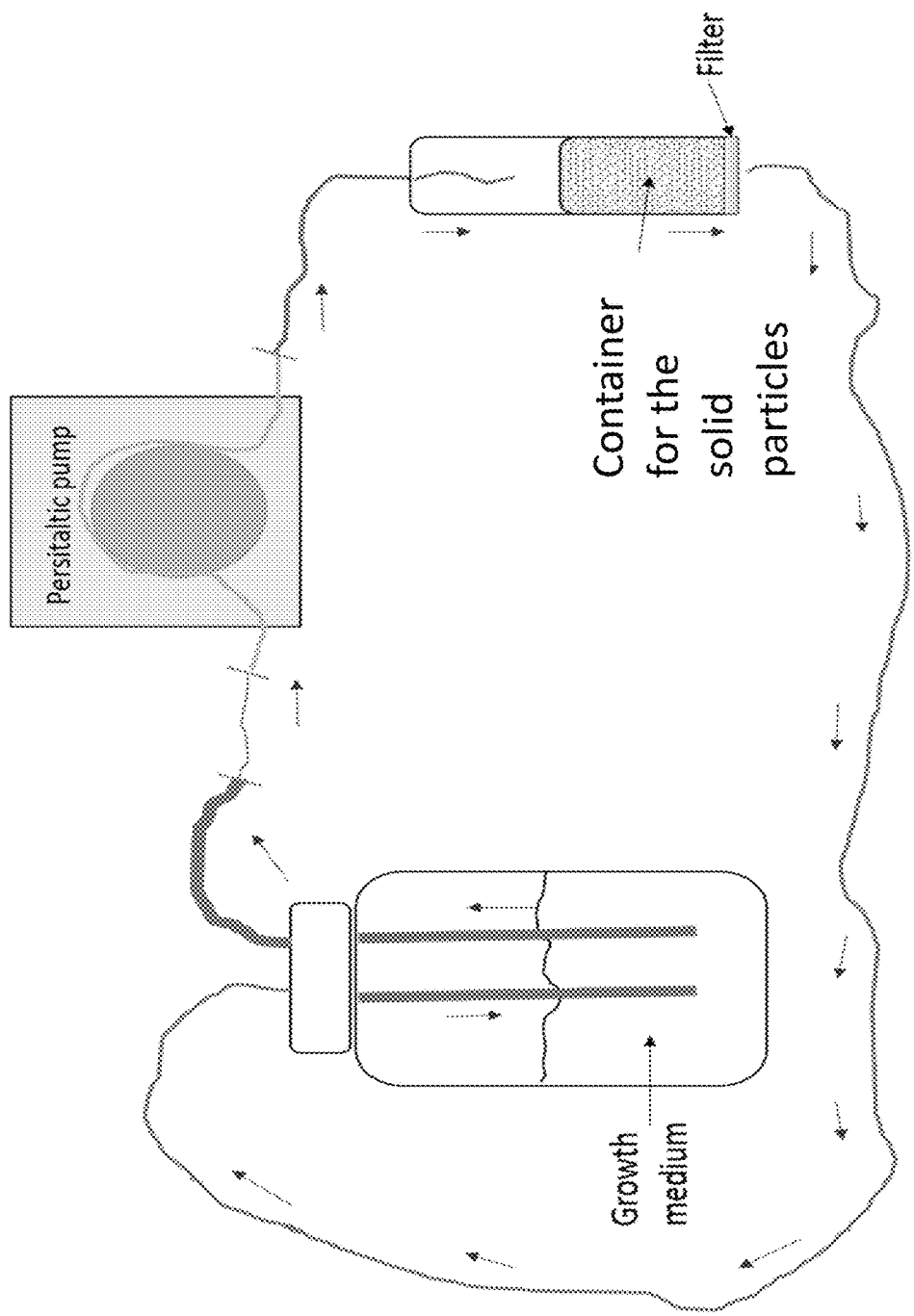
FIG. 1 shows an illustration of an exemplary embodiment of the present invention, showing a flow system used according to the methods according to some embodiments of the present invention.

For clarity of disclosure, and not by way of limitation, the detailed description of the invention is divided into the following subsections that describe or illustrate certain features, embodiments or applications of the present invention.

Throughout the specification and claims, the following terms take the meanings explicitly associated herein, unless the context clearly dictates otherwise. The phrases "in one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments of the invention may be readily combined, without departing from the scope or spirit of the invention.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on."

In some embodiments, the present invention relates to system and method for growing and encapsulating at least one strain of bacteria in a biofilm form, configured for pH dependent targeted release of the bacterial biofilm in the gastrointestinal tract.

In one embodiment, the present invention provides a method,
wherein the method forms a biofilm,
wherein the biofilm comprises a population of at least one bacterial strain attached to particles,
wherein the biofilm is configured to colonize a gut of a subject in need thereof for at least five days, when ingested by the subject, the method comprising:
a. obtaining a population comprising at least one strain of bacteria;
b. inoculating a growth medium containing particles with the population comprising at least one strain of bacteria;
c. incubating the particles with the population comprising at least one bacterial strain for a time sufficient for the population of at least one strain of bacteria to attach to the particles; and
d. culturing the population comprising at least one strain of bacteria attached to the particles in a growth medium, for a time sufficient to form a biofilm.

In some embodiments, the time sufficient for the population of at least one strain of bacteria to attach to the particles is from 2 hours to 12 hours. In some embodiments, the time sufficient for the population of at least one strain of bacteria to attach to the particles is 2 hours. In some embodiments, the time sufficient for the population of at least one strain of bacteria to attach to the particles is 4 hours. In some embodiments, the time sufficient for the population of at least one strain of bacteria to attach to the particles is 6 hours. In some embodiments, the time sufficient for the population of at least one strain of bacteria to attach to the particles is 8 hours. In some embodiments, the time sufficient for the population of at least one strain of bacteria to attach to the particles is 10 hours. In some embodiments, the time sufficient for the population of at least one strain of bacteria to attach to the particles is 12 hours.

In some embodiments, the time sufficient to form a biofilm is from 12 hours to 48 hours. In some embodiments, the time sufficient to form a biofilm is 12 hours. In some embodiments, the time sufficient to form a biofilm is 14 hours. In some embodiments, the time sufficient to form a biofilm is 16 hours. In some embodiments, the time sufficient to form a biofilm is 18 hours. In some embodiments, the time sufficient to form a biofilm is 20 hours. In some embodiments, the time sufficient to form a biofilm is 22 hours. In some embodiments, the time sufficient to form a biofilm is 24 hours. In some embodiments, the time sufficient to form a biofilm is 26 hours. In some embodiments, the time sufficient to form a biofilm is 28 hours. In some embodiments, the time sufficient to form a biofilm is 30 hours. In some embodiments, the time sufficient to form a biofilm is 32 hours. In some embodiments, the time sufficient to form a biofilm is 34 hours. In some embodiments, the time sufficient to form a biofilm is 36 hours. In some embodiments, the time sufficient to form a biofilm is 38 hours. In some embodiments, the time sufficient to form a biofilm is 40 hours. In some embodiments, the time sufficient to form a biofilm is 42 hours. In some embodiments, the time sufficient to form a biofilm is 44 hours. In some embodiments, the time sufficient to form a biofilm is 46 hours. In some embodiments, the time sufficient to form a biofilm is 48 hours.

In some embodiments, the population of at least one strain of bacteria attached to the particles is cultured in the growth medium under flow conditions. As used herein, the term "flow conditions" refers to the movement of culture medium in relation to bacteria attached to a surface, wherein the movement of the culture medium exerts a shear force on the bacteria.

Without intending to be limited to any particular theory, culturing the population of at least one strain of bacteria attached to the particles under flow conditions creates even gentle shear forces on the growing biofilm and increases the fast creation of the biofilm (e.g., in a shorter period of time compared with typical stationary growth methods). In some embodiments, a flowing system allows for the introduction of fresh culture medium to the growing biofilm, and the removal of bacterial waste.

In some embodiments, the flow conditions comprise a flow rate of 10 ml/hour to 100 ml/hour. In some embodiments, the flow conditions comprise a flow rate of 20 ml/hour. In some embodiments, the flow conditions comprise a flow rate of 30 ml/hour. In some embodiments, the flow conditions comprise a flow rate of 40 ml/hour. In some embodiments, the flow conditions comprise a flow rate of 50 ml/hour. In some embodiments, the flow conditions comprise a flow rate of 60 ml/hour. In some embodiments, the flow conditions comprise a flow rate of 70 ml/hour. In some embodiments, the flow conditions comprise a flow rate of 80 ml/hour. In some embodiments, the flow conditions comprise a flow rate of 90 ml/hour. In some embodiments, the flow conditions comprise a flow rate of 100 ml/hour. In some embodiments, the flow conditions comprise a flow rate of 10 ml/hour.

In some embodiments, the flow conditions comprise shaking the culture of bacteria from 90 to 150 rpm. In some embodiments, the flow conditions comprise shaking the culture of bacteria at 100 rpm. In some embodiments, the flow conditions comprise shaking the culture of bacteria at 110 rpm. In some embodiments, the flow conditions comprise shaking the culture of bacteria at 120 rpm. In some embodiments, the flow conditions comprise shaking the culture of bacteria at 130 rpm. In some embodiments, the flow conditions comprise shaking the culture of bacteria at 140 rpm. In some embodiments, the flow conditions comprise shaking the culture of bacteria at 150 rpm.

In some embodiments, culturing the population of at least one strain of bacteria attached to the particles under flow conditions results in producing a robust and healthy biofilm in a shorter period of time compared with typical methods (e.g., but not limited to, 5, 10, 20, 25, 50% less time). In some embodiments, the resulting biofilm has an increased resilience to harsh conditions when compared with other culturing methods, and is further detailed herein.

Referring to FIG. 1, an illustration of an exemplary embodiment of the present invention, showing a flow system according to some embodiments of the present invention is shown. Referring to FIG. 1, the system includes a container that contains the solid particles for biofilm cultivation, a source of growth medium, tubes that conduct the growth medium in and out of the container, and a pump that moves the medium through the tubes. The fluid outlet from the container can return to the medium reservoir for recycling, or can be drained away. In some embodiments, this flow system can be closed, open, or semi-closed. The clockwise moving arrows in FIG. 1 represent the direction of the flow, and are for illustration purposes only.

In some embodiments, the population of at least one strain of bacteria attached to the particles is cultured in the growth medium under static conditions. As used herein, the term "static conditions" refers to culture conditions where no shear forces exerted on the bacteria.

In some embodiments, the population of at least one strain of bacteria attached to the particles is first cultured in the growth medium under static conditions, followed by culture in the growth medium under flow conditions.

In some embodiments, the population of at least one strain of bacteria attached to the particles is cultured under anaerobic conditions. As used herein, the term "anaerobic conditions" refers to culture conditions comprising the absence of free or bound oxygen.

In some embodiments, the population of at least one strain of bacteria attached to the particles is cultured under aerobic conditions. As used herein, the term "aerobic conditions" refers to culture conditions comprising the presence of free or bound oxygen.

Particles

In some embodiments, the particles are porous, and selected from the group consisting of: seeds, dicalcium phosphate, clay, sand, and cellulose.

In some embodiments, the seeds are selected from the group consisting of: pomegranate seeds, and passion fruit seeds. In some embodiments, the seeds are crushed.

In some embodiments, the cellulose particles comprise cellulose sold under the tradename AVICEL® (microcrystalline cellulose or MCC). In some embodiments, the cellulose particles comprise cellulose sold under the tradename SOLKA®.

In some embodiments, a plurality of particles is used in the method to form a biofilm according to some embodiments of the present invention. In some embodiments, the particles range from 5 microns to 1 cm in diameter. In some embodiments, the particles are 5 microns in diameter. In some embodiments, the particles are 10 microns in diameter. In some embodiments, the particles are 15 microns in diameter. In some embodiments, the particles are 20 microns in diameter. In some embodiments, the particles are 30 microns in diameter. In some embodiments, the particles are 40 microns in diameter. In some embodiments, the particles are 50 microns in diameter. In some embodiments, the particles are 60 microns in diameter. In some embodiments, the particles are 70 microns in diameter. In some embodiments, the particles are 80 microns in diameter. In some embodiments, the particles are 90 microns in diameter. In some embodiments, the particles are 100 microns in diameter. In some embodiments, the particles are 200 microns in diameter. In some embodiments, the particles are 300 microns in diameter. In some embodiments, the particles are 400 microns in diameter. In some embodiments, the particles are 500 microns in diameter. In some embodiments, the particles are 600 microns in diameter. In some embodiments, the particles are 700 microns in diameter. In some embodiments, the particles are 800 microns in diameter. In some embodiments, the particles are 900 microns in diameter. In some embodiments, the particles are 1 cm in diameter.

Bacterial Strains

In some embodiments, the population comprising at least one bacterial strain is derived from intestinal flora.

In some embodiments, the population comprising at least one bacterial strain is a probiotic strain. As used herein, the term "probiotic" refers to a bacterial strain that stimulates the growth of microorganisms, especially those with beneficial properties (such as those of the intestinal flora).

In some embodiments, the population comprising at least one bacterial strain is *Lactobacillus plantarum*.

In some embodiments, the population comprising at least one bacterial strain is *Acetobacter pomorum*.

In some embodiments, the biofilm formed by the method is configured for pH dependent targeted release of the bacterial biofilm in the gastrointestinal tract.

In some embodiments, the biofilm comprises two or more strains of bacteria.

Figure 2A:
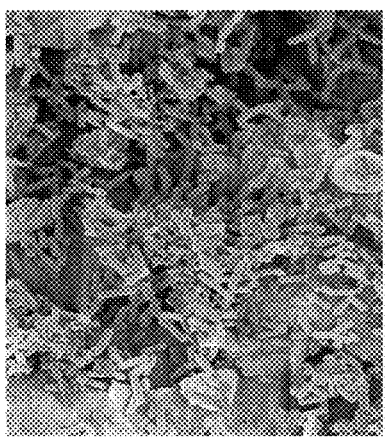
FIG. 2A to 2C show images of some exemplary embodiments of biofilms generated by the methods according to some embodiments of the present invention.
Figure 2A:
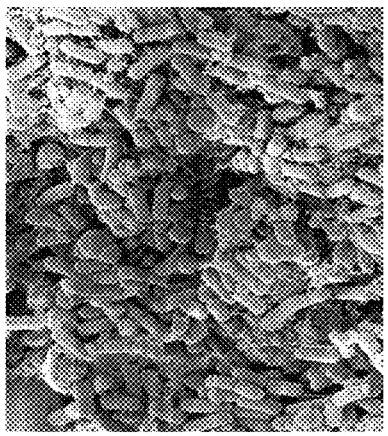
Figure 2A:
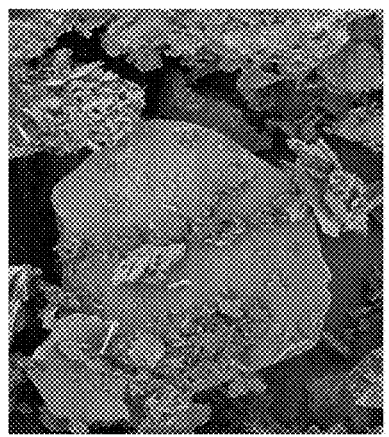
Figure 2A:
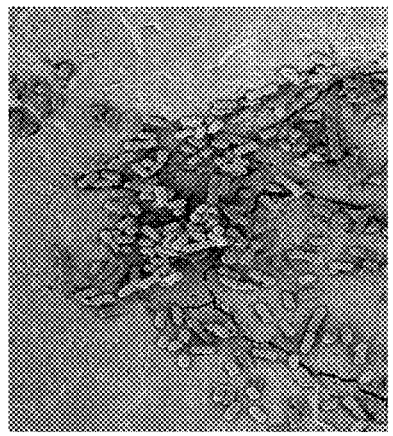
Figure 2A:
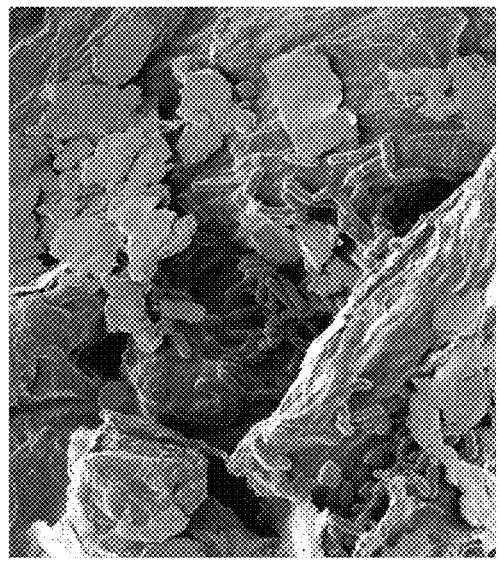
Figure 2A:
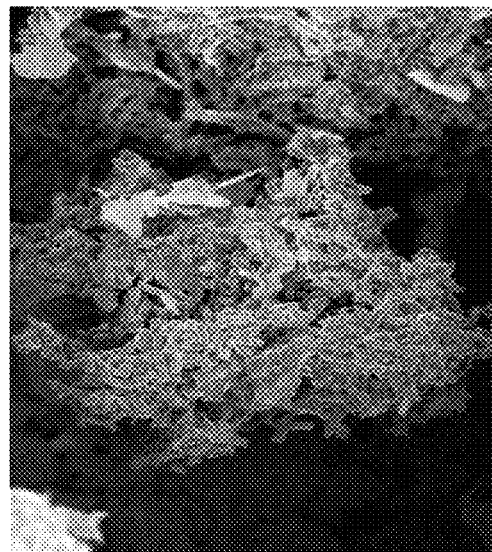
Figure 2A:
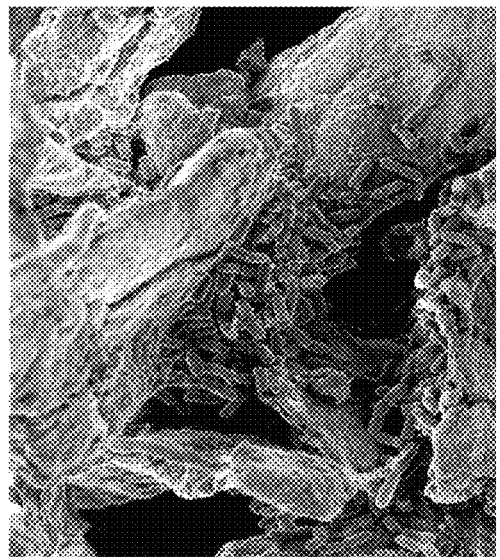

FIG. 2A shows images of some exemplary embodiments of biofilms generated by the methods of the present invention. In some embodiments, several types of solid particles appropriate for growing probiotic bacteria have been tested and the results are shown herein. FIG. 2A shows electron microscope images of *Lactobacillus plantarum* biofilm grown on different solid particles, such as, for example, passion fruit seeds, pomegranate crushed seeds, bentonite clay, sand particles, white clay, SOLKA® fibers, dicalcium phosphate (DCP), AVICEL®. With the exception of white clay, bacteria grow on all particle types.

Figure 2B:
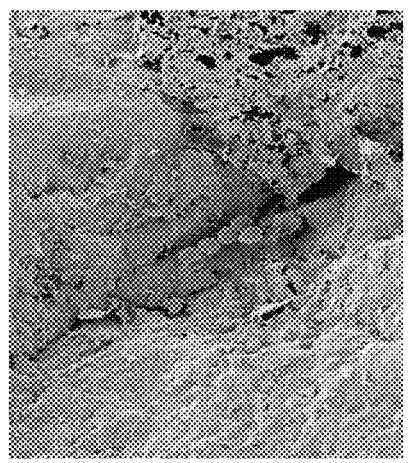
Figure 2B:
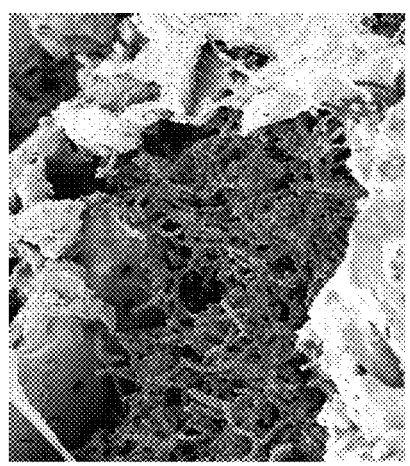
Figure 2B:
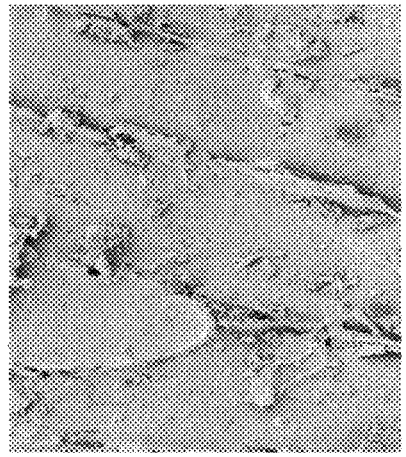
Figure 2C:
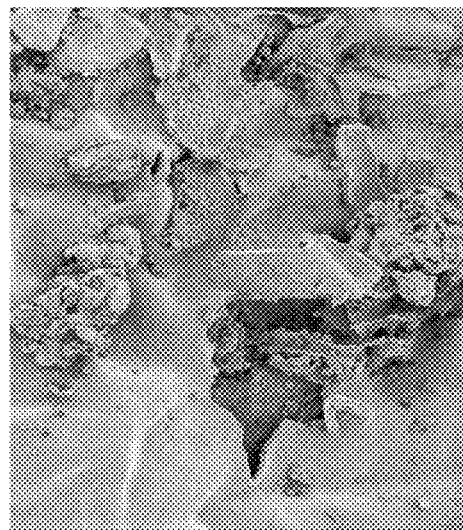
Figure 2C:
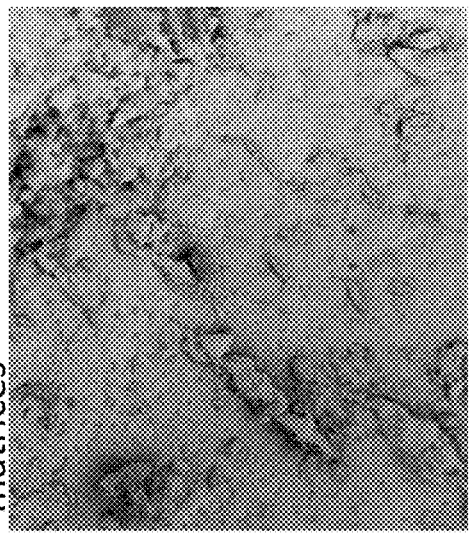

FIG. 2B shows images of some exemplary embodiments of biofilms generated by the methods of the present invention, showing the biofilm growth of *Acetobacter pomorum* on passion fruit crushed seeds, pomegranate crushed seeds, and sand. *Acetobacter pomorum* grew and formed a biofilm on pomegranate seeds. However, very little growth on sand was observed. *Acetobacter pomorum* did not grow on passion fruit seeds. Other bacteria species tested, for example *Pseudomonas* spp, did not grow on the solid particles tested, as shown in FIG. 2C.

Without being bound by theory, different particles provide distinguishable microenvironments for the bacteria to grow on, such as pore size, roughness of the surface, nutrients available in the particles, viscosity, surface charge, etc., which may influence the ability of various bacteria to attach and grow on various kinds of particles.

In some embodiments of the methods of the present invention, the method
  generates a biofilm containing at least two strains of probiotic bacteria (e.g., but not limited to, 2, 3, 4, 5, 6, 7, 8, 9, 10, etc.), where the biofilm is generated using a combination of at least two different particles (e.g., but not limited to, passion fruit seeds, pomegranate crushed seeds, etc.). In some embodiments, for creating such combinations, the growth conditions (and, e.g., but not limited to types of particle(s)) are selected according to the strain(s) for use in generating a biofilm. In an exemplary embodiment, if two bacterial strains will eventually be combined to generate a biofilm, each of the bacterial strains will be grown using the particle best suited for the growth of each strain. In some embodiments, when two or more bacterial strains are grown separately, the bacterial strains are combined during the encapsulation process.

Treatment

In some embodiments, a biofilm is administered to an animal in need thereof, to colonize the gut of the animal with the biofilm.

In some embodiments, the biofilm comprising a population of at least one bacterial strain attached to particles is encapsulated with a compound configured to release the at least one bacterial strain at a pH found in the intestine of the animal.

In some embodiments, the compound configured to release the at least one bacterial strain at a pH found in the intestine of the animal is alginate.

In some embodiments, the pH found in the intestine of the animal is pH 8.

In some embodiments, the biofilm is administered to an animal in need thereof in an amount sufficient to colonize the gut. In some embodiments, colonization is confirmed by the presence of the at least one population of bacteria being present in the feces of the animal for at least 5 days post administration.

In some embodiments, the colonized bacteria derived from the biofilm can inhabit the gut of a mammal for at least one week (e.g., but not limited to, 2, 3, 4, 5, 6, 7, 8, 9, 10, etc. weeks). In some embodiments, the colonized bacteria derived from the biofilm are sustainable within a mammalian gut, i.e., do not die off after 3 days.

In some embodiments, the amount sufficient to colonize the gut is $2\times10^4$ to $2\times10^9$ bacteria per day, for 1 to 5 days. In some embodiments, the amount sufficient to colonize the gut is $2\times10^4$ to $2\times10^6$ bacteria per day, for 1 to 5 days.

In some embodiments, the amount sufficient to colonize the gut is $2\times10^4$ bacteria per day, for 5 days. In some embodiments, the amount sufficient to colonize the gut is $2\times10^5$ bacteria per day, for 5 days. In some embodiments, the amount sufficient to colonize the gut is $2\times10^6$ bacteria per day, for 5 days. In some embodiments, the amount sufficient to colonize the gut is $2\times10^7$ bacteria per day, for 5 days. In some embodiments, the amount sufficient to colonize the gut is $2\times10^8$ bacteria per day, for 5 days. In some embodiments, the amount sufficient to colonize the gut is $2\times10^9$ bacteria per day, for 5 days.

In some embodiments, the amount sufficient to colonize the gut is $2\times10^4$ bacteria per day, for 4 days. In some embodiments, the amount sufficient to colonize the gut is $2\times10^5$ bacteria per day, for 4 days. In some embodiments, the amount sufficient to colonize the gut is $2\times10^6$ bacteria per day, for 4 days. In some embodiments, the amount sufficient to colonize the gut is $2\times10^7$ bacteria per day, for 4 days. In some embodiments, the amount sufficient to colonize the gut is $2\times10^8$ bacteria per day, for 4 days. In some embodiments, the amount sufficient to colonize the gut is $2\times10^9$ bacteria per day, for 4 days.

In some embodiments, the amount sufficient to colonize the gut is $2\times10^4$ bacteria per day, for 3 days. In some embodiments, the amount sufficient to colonize the gut is $2\times10^5$ bacteria per day, for 3 days. In some embodiments, the amount sufficient to colonize the gut is $2\times10^6$ bacteria per day, for 3 days. In some embodiments, the amount sufficient to colonize the gut is $2\times10^7$ bacteria per day, for 3 days. In some embodiments, the amount sufficient to colonize the gut is $2\times10^8$ bacteria per day, for 3 days. In some embodiments, the amount sufficient to colonize the gut is $2\times10^9$ bacteria per day, for 3 days.

In some embodiments, the amount sufficient to colonize the gut is $2\times10^4$ bacteria per day, for 2 days. In some embodiments, the amount sufficient to colonize the gut is $2\times10^5$ bacteria per day, for 2 days. In some embodiments, the amount sufficient to colonize the gut is $2\times10^6$ bacteria per day, for 2 days. In some embodiments, the amount sufficient to colonize the gut is $2\times10^7$ bacteria per day, for 2 days. In some embodiments, the amount sufficient to colonize the gut is $2\times10^8$ bacteria per day, for 2 days. In some embodiments, the amount sufficient to colonize the gut is $2\times10^9$ bacteria per day, for 2 days.

In some embodiments, the amount sufficient to colonize the gut is $2\times10^4$ bacteria per day, for 1 day. In some embodiments, the amount sufficient to colonize the gut is $2\times10^5$ bacteria per day, for 1 day. In some embodiments, the amount sufficient to colonize the gut is $2\times10^6$ bacteria per day, for 1 day. In some embodiments, the amount sufficient to colonize the gut is $2\times10^7$ bacteria per day, for 1 day. In some embodiments, the amount sufficient to colonize the gut is $2\times10^8$ bacteria per day, for 1 day. In some embodiments, the amount sufficient to colonize the gut is $2\times10^9$ bacteria per day, for 1 day.

In some embodiments, the amount sufficient is administered on a single particle. Alternatively, the amount sufficient is administered on a plurality of particles.

In some embodiments, the amount sufficient is mixed with food, and ingested.

In some embodiments, the biofilm is administered to the animal immediately after the biofilm is cultured. Alternatively, the biofilm may be stored, prior to administration. The biofilm may be stored frozen, or, alternatively, in a lyophilized form.

Reference is now made to the following examples, which together with the above descriptions illustrate some embodiments of the invention in a non-limiting fashion.

EXAMPLES

Example 1: Acidity Tolerance of a Biofilm According to Some Embodiments of the Present Invention The resilience of the biofilm grown on solid particles in the flowing system as described above was tested. Specifically, the first parameter tested was acidity tolerance, and the results are shown in FIG. 3.

An overnight culture of *L. plantarum* was inoculated in pomegranate matrix soaked in 25% MRS medium (to encourage biofilm formation, starvation conditions (i.e. less than a 100% concentration of growth medium) were used) in the matrix container and left still for 2.5 hours (i.e., no mixing), and then the flow system was initiated. Medium was moved from the medium reservoir to the matrix container using a peristaltic pump at a speed of 12 ml/hour for a duration of 5 days. The medium was not recycled. Fresh medium entered the culture and the outlet drained away the used media. As a control, bacteria grown planktonically (i.e., not attached to a particle) were used, resulting in a lack of biofilm forming. For the planktonic control, 4-5 colonies of *L. plantarum* were inoculated in 6 ml of 100% MRS broth and left still in incubator at 37° C. overnight.

To test acidity tolerance, a series of vials with PBS adjusted to increasing pH using HCl (stock solution 0.5M) prepared in advance to create pH 1, 2, 3, and 2 grams of the particles having a biofilm was transferred into the vials and incubated for 1 hr. The bacteria were then washed in PBS and 5 microliters were plated as shown in FIG. 3.

Figure 3:
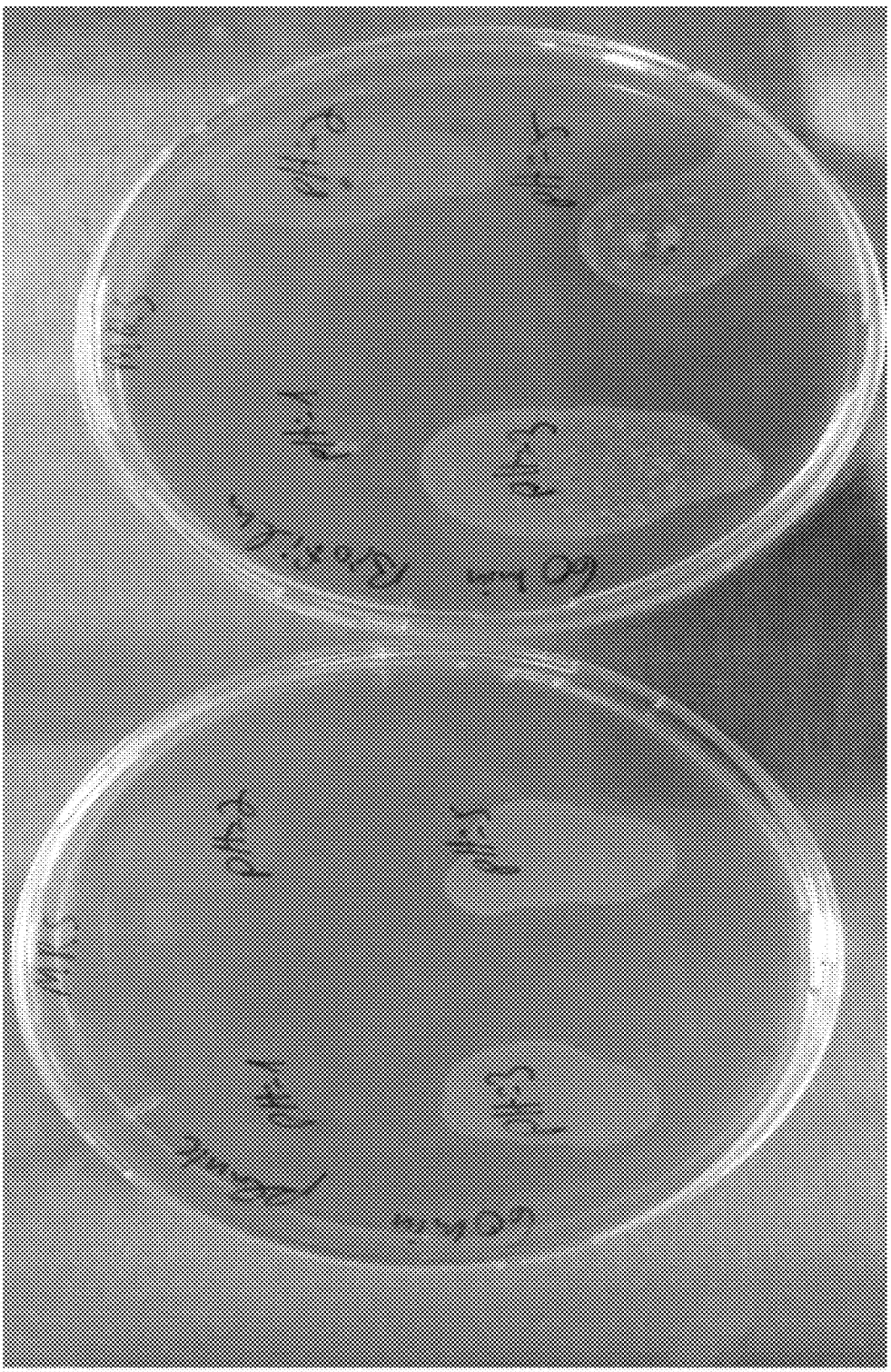
FIG. 3 shows the acidity tolerance of a biofilm according to some embodiments of the present invention.

For the planktonic control, 100 μl from the overnight culture were taken into the pH vials and incubated for 1 hr, the bacteria were then washed in PBS and 5 microliters were plated as shown in FIG. 3. As shown in FIG. 3, the biofilm bacteria show a greater resilience to acidity as they survived well pH 2, while the planktonic bacteria did not survive.

Without intending to be limited to any particular theory, the pH in the stomach is about pH 2. Thus, upon administration of the biofilm to a subject, the biofilm will survive the subject's stomach environment (i.e., pH of 2) and colonize the subject.

Example 2: Acidity Tolerance of Another Biofilm According to Some Embodiments of the Present Invention A second set of experiments were conducted and demonstrate bacterial resilience to acidity (i.e., in the form of a biofilm) is described in FIG. 4 and shown in Tables 1 and 2 below.

An overnight culture of L. plantarum was inoculated into 7 grams of pomegranate (POM) seed particles soaked in 25% MRS medium (starvation conditions), and left still for 2.5 hours. Next, the flowing system was conducted for 5 days, using a peristaltic pump that moved the medium at max speed (about 380 ml/hour). In this experiment, the medium was recycled, to compare to the non flowing/stationary control. For planktonic control, 4 colonies of L. plantarum were inoculated in 6 ml of 100% MRS broth and left in incubator 37° C. overnight+5 hours. Results are shown in Tables 1 and 2.

TABLE 1

Cell Growth

| pH | Planktonic (cells/ml) | | Biofilm flow (cells/1 gr matrix) | |
|---|---|---|---|---|
| 1.5 | $2 * 10^4$ | $2.3 * 10^4$ | — | — |
| 2 | $5.6 * 10^3$ | $3.3 * 10^3$ | $5 * 10^8$ | $4 * 10^8$ |
| 2.5 | $3 * 10^6$ | $6.6 * 10^6$ | $4.5 * 10^8$ | $5.6 * 10^8$ |
| 3 | $6.3 * 10^8$ | $6.3 * 10^8$ | $4.3 * 10^8$ | $5.1 * 10^8$ |
| 4 | $6.3 * 10^8$ | $4 * 10^8$ | $10^9$ | $1.3 * 10^9$ |
| 7.4 | $1.1 * 10^9$ | $1.1 * 10^9$ | $3 * 10^8$ | $3.8 * 10^8$ |

TABLE 2

Figure 4:
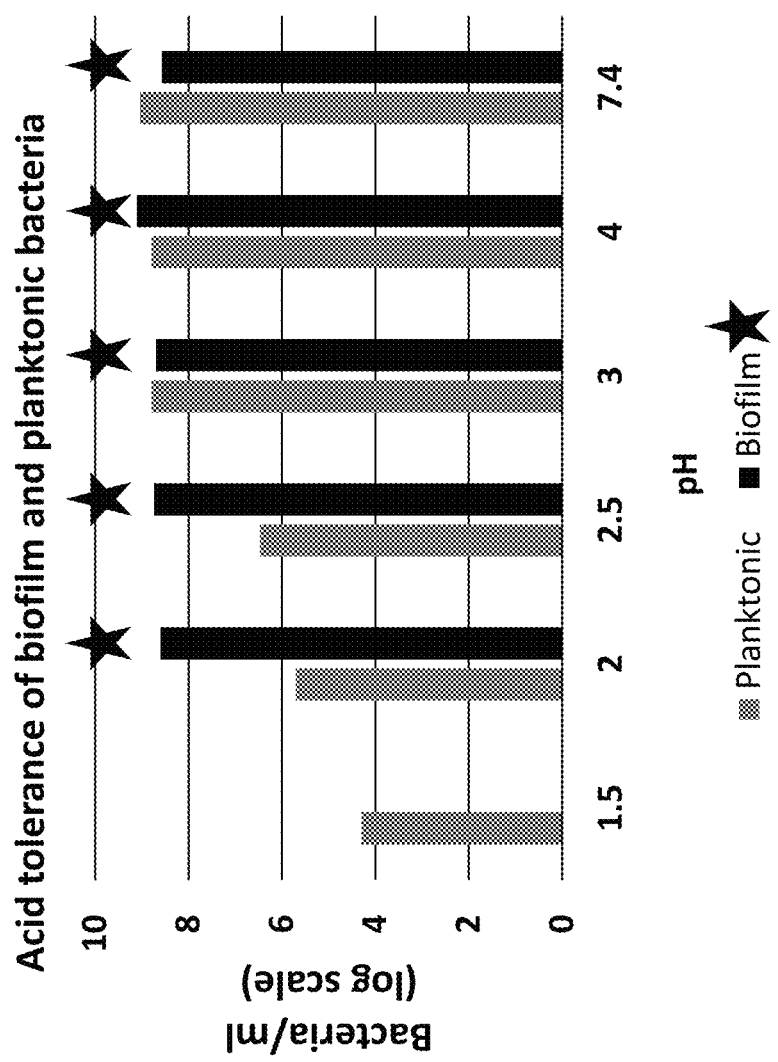
FIG. 4 shows the acidity tolerance of another biofilm according to some embodiments of the present invention.

Data of Figure 4 (Log of Results)

| pH | Planktonic (cells/ml) | | Biofilm flow (cells/1 gr matrix) | |
|---|---|---|---|---|
| 1.5 | 4.3 | 4.36 | — | — |
| 2 | 5.7 | 5.51 | 8.69 | 8.6 |
| 2.5 | 6.47 | 6.81 | 8.65 | 8.74 |
| 3 | 8.79 | 8.79 | 8.63 | 8.7 |
| 4 | 8.79 | 8.6 | 9 | 9.11 |
| 7.4 | 9.04 | 9.04 | 8.47 | 8.57 |

As shown in FIG. 4, the planktonic bacteria showed decreasing survival when exposed to decreasing pH.

Figure 5:
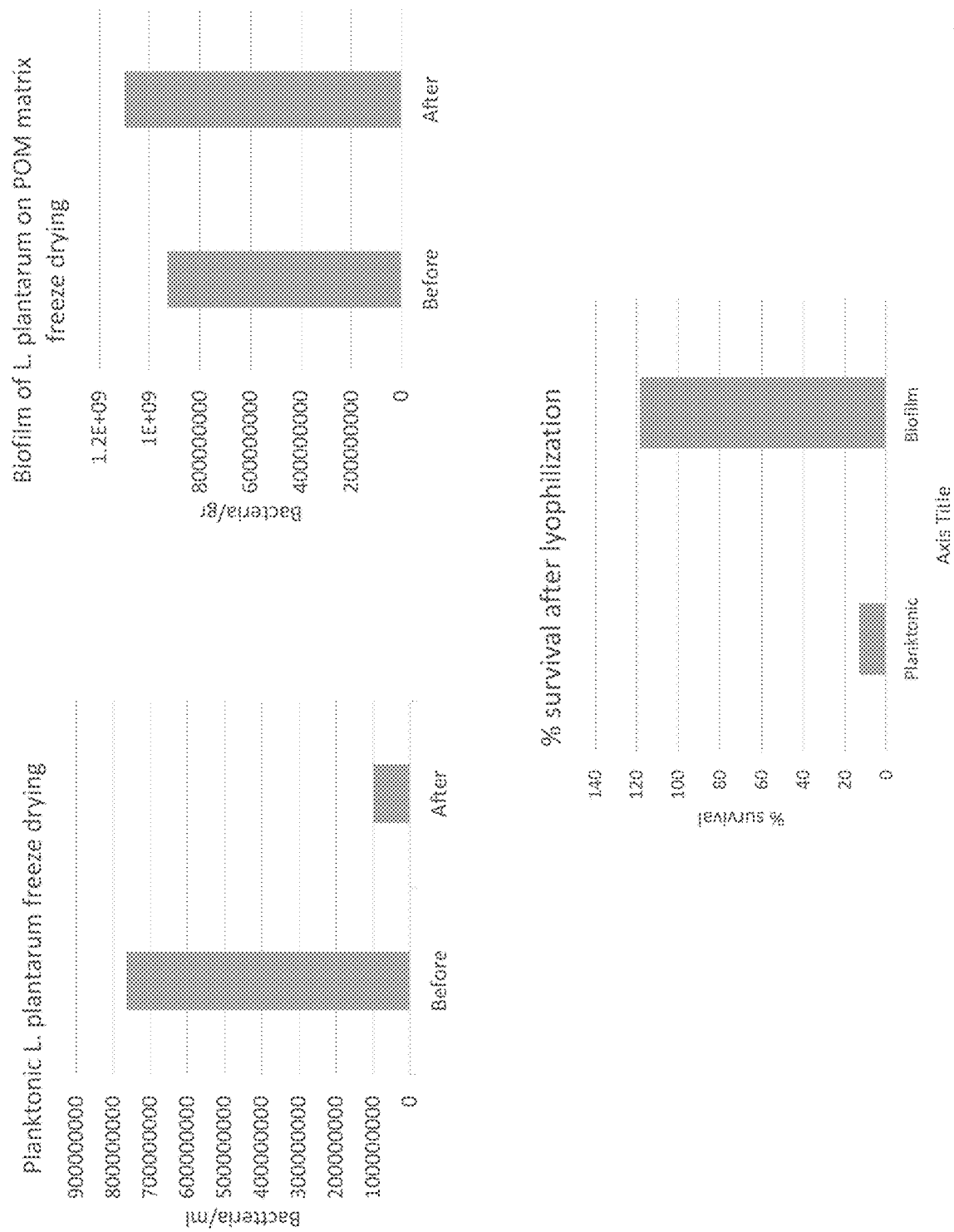
FIG. 5 shows the tolerance of a biofilm according to some embodiments of the present invention to lyophilization.

Example 3: Reconstitution of a Biofilm According to Some Embodiments of the Present Invention The biofilm grown and entrapped in alginate recovered after drying. L. plantarum was grown in 25 ml 100% MRS+2 gr POM for 4 days at room temperature to form biofilms. For planktonic control, L. plantarum was grown in 25 ml 100% MRS for 4 days at room temp. One sample of POM+biofilm and control were plated on MRS plates in serial dilutions. Another sample of each was centrifuged briefly, resuspended in 5 ml freeze drying buffer, lyophilized for 24 hours, and suspended in 25 mL MRS. At this stage (after lyophilization but before further growth), samples were plated by serial dilutions. The remainder of the sample was left to grow for 48 additional hours, and plated again. As shown in FIG. 5, bacteria that grew as biofilm on solid particles showed an enhanced resistance and survival to lyophilization (i.e., reconstitution after drying).

Example 4: Acid Tolerance of E. coli DH5α Cells

Acid tolerance of E. coli strain DH5a was tested under three conditions:
1. Planktonic—E. coli grown in 20 ml LB starter in shaker for 5 days at 23° C.
2. Biofilm static—E. coli grown in 20 ml LB with 2 gr of different matrixes grown for 5 days in static conditions at 37° C.
3. Biofilm flow—E. coli grown in column flow system with DCP for 5 days at room temperature at a speed of approximately 12 ml/hour fresh 25% LB. Samples were taken from the top of the column (close to the air surface) and from the bottom of the column.

E. coli strain DH5a starter was grown overnight in 37° C. shaking. 100 µl from the starter was transferred to:
1. 1.2 gr AVICEL®+20 ml LB—for biofilm static culture.
2. 2.2 gr SOLKA® fibers+20 ml LB—for biofilm static culture.
3. 3.3 gr DCP+20 ml LB—for biofilm static culture.
4. 4.20 ml LB—for planktonic culture.

2 ml of the overnight starter was transferred to 20 ml of LB and inoculated in the column of the flow system. Flow was arrested for 2 hours to let the E. coli attach to the DCP. After 2 hours, flow was turned on for 5 days at room temperature.

After 5 days of incubation, a sample from each of the matrixes from the static experiments (DCP, AVICEL® and SOLKA®) and a sample from the DCP form the top of the column and DCP form the bottom of the column was taken and inserted into five different Eppendorf tubes ("Eppendorfs"). The samples were gently washed once with PBS.

From each sample, the following amount of matrix was taken into two vials:
5. 1. Static DCP—0.02 gr
6. 2. Static AVICEL®—0.03 gr
7. 3. Static SOLKA®—0.02 gr
8. 4. Flow DPC top—0.03 gr
9. 5. Flow DCP bottom—0.03 gr The content of each Eppendorf was gently washed once with PBSX1. For each pair of eppendorfs (from each sample), 1 ml of PBSX1 (pH=7.4) or 1 ml of PBS (pH=2) was added. The eppendorfs were incubated on their side for 1 hour at room temp. The eppendorfs were then centrifuged at 13,000 rpm for 2 min, the supernatant was discarded. 1 ml of PBSX1 was added to each Eppendorf and the eppendorfs were vortexed at full power for 30 sec to free the bacteria from the matrix.

Handling of the planktonic culture: 1 ml of culture was transferred to an Eppendorf and centrifuged at full speed for 2 min. Supernatant was discarded and 1 ml of PBS was added. 100 µl from this was added to:
1. Eppendorf with 1 ml of PBSX1 (pH=7.4)
2. Eppendorf with 1 ml of PBS (pH=2)

The eppendorfs were incubated for 1 hour at room temp on their side, and this incubation was followed by centrifugation at 13,000 rpm for 2 min. 100 µl of PBSX1 was added to each Eppendorf.

Viable Counts:

10 μl from each eppendorf was transferred to 90 μl of PBSX1. Seven 1:10 serial dilutions were conducted. 4l from each dilution were plated on an LB plate and left in the incubator overnight.

The calculations were as follows to retain bacteria/ml for planktonic or bacteria/gr:

For matrices: Number of colonies× $10^{dilution\ number}$×333.33×(1/gr taken)

For planktonic: Number of colonies× $10^{dilution\ number}$×333.3

Figure 6:
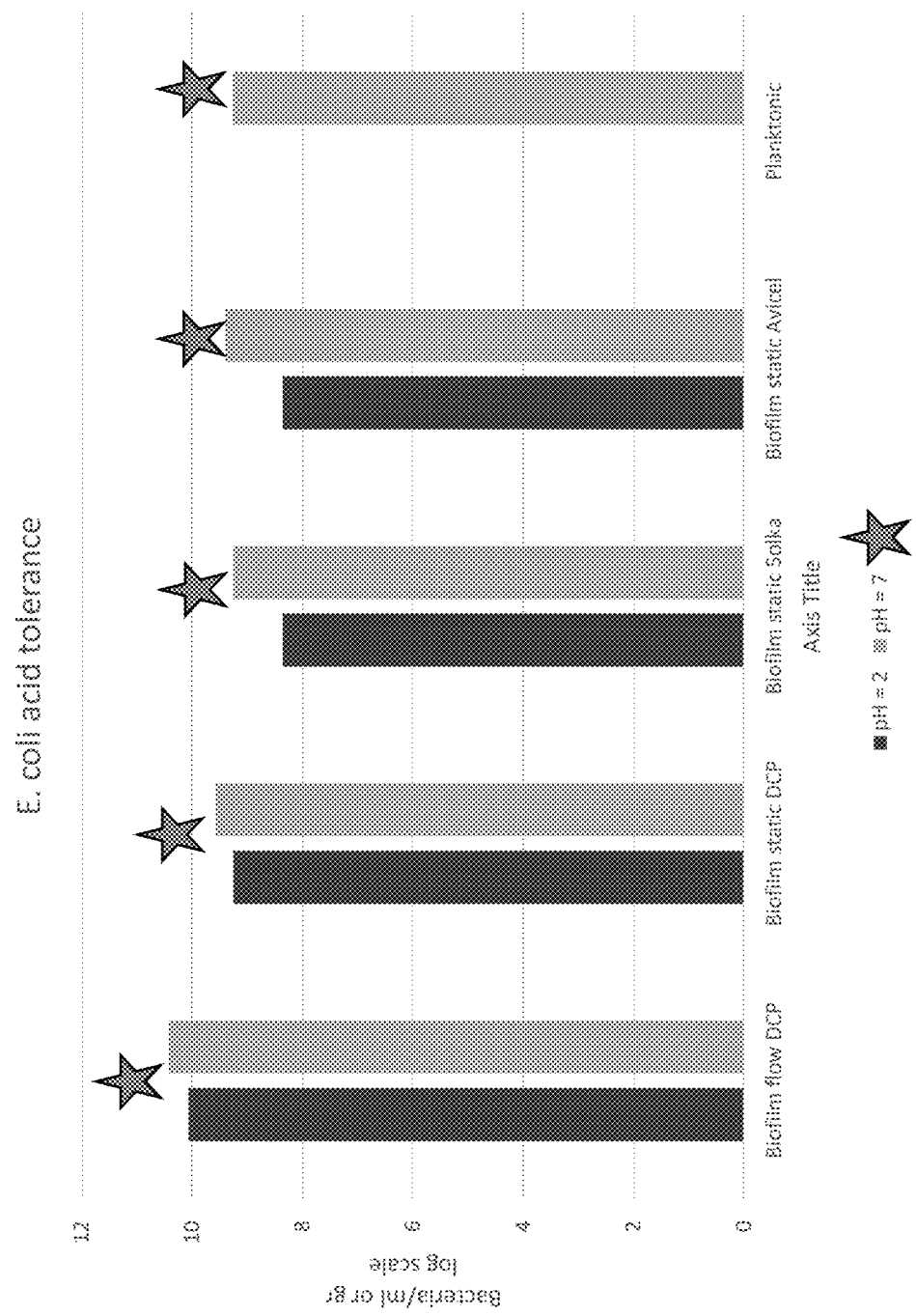
FIG. 6 shows the acidity tolerance of another biofilm according to some embodiments of the present invention.

All materials in this experiment were autoclaved for sterilization. The results as shown in the tables below and in FIG. 6 demonstrate that the biofilm increased the acid tolerance of the bacteria, in the static conditions and exhibited a greater increase in the flow conditions.

TABLE 3

Results (*E. coli* DH5α):

|  | pH = 2 | pH = 7 | % survival in pH 2 |
|---|---|---|---|
| Top flow biofilm DCP | 1.2 * $10^{10}$ bacteria/gr | 2.7 * $10^{10}$ bacteria/gr | 44.4% |
| Bottom flow biofilm DCP | 6.6 * $10^9$ bacteria/gr | 1.4 * $10^{10}$ bacteria/gr | 47.1% |
| Static biofilm DCP | 1.8 * $10^9$ bacteria/gr | 3.8 * $10^9$ bacteria/gr | 47.36% |
| Static biofilm Solka | 2.3 * $10^8$ bacteria/gr | 1.8 * $10^9$ bacteria/gr | 12.7% |
| Static biofilm Avicel | 2.3 * $10^8$ bacteria/gr | 2.6 * $10^9$ bacteria/gr | 8.8% |
| Planktonic | 0 bacteria/ml | 1.9 * $10^9$ bacteria/ml | 0% |

TABLE 4

| | Log Scale | | |
|---|---|---|---|
| | pH = 2 | pH = 7 | % survival in pH 2 |
| Top flow biofilm DCP | 10.07 | 10.43 | 44.4% |
| Bottom flow biofilm DCP | 9.8 | 10.14 | 47.1% |
| Static biofilm DCP | 9.25 | 9.57 | 47.36% |
| Static biofilm Solka | 8.36 | 9.25 | 12.7% |
| Static biofilm Avicel | 8.36 | 9.41 | 8.8% |
| Planktonic | 0 | 9.27 | 0% |

Example 5: Colonization of Murine Gut Using a Composition According to Some Embodiments of the Present Invention To test whether the bacteria grown as biofilm show enhanced ability to colonize the gut, biofilm was prepared as described above, and the biofilm fed to nude mice. The presence of bacteria in the mouse feces was tested. The results are shown in FIG. 7.

Protocol:
1. 6 germ-free mice
2. *Lactobacillus plantarum* biofilm grown on matrix.
3. Ground food for mice mixed with sterile matrix only (Grind together).
4. Ground food for mice mixed with *L. plantarum* biofilm on matrix (Grind together).
5. Ground food for mice mixed with *L. plantarum* biofilm in alginate beads.
6. Live-dead staining kit (to determine presence of live bacteria).
7. Autoclave matrix for control mice.
8. The mice were divided into 3 groups (2 mice for each group):
    a. Control—mice that are fed food+matrix only.
    b. Biofilm—mice that are fed with food+biofilm on matrix.
    c. Biofilm alginate—mice that are fed with food+ biofilm on matrix in alginate beads.
9. Feed mice with corresponding food for 7 days (D1-D7).
10. Sample stool at day 8 (D8), day 9 (D9), day 10 (D10), Day 11 (D11), day 12 (D12), day 13 (D13) and day 14 (D14).
11. Check presence of *L. plantarum* in stool samples.
12. Take section from inner intestine to image biofilm of *L. Plantarum* on intestine, and stain for live-dead using a designated staining kit.

Figure 7:
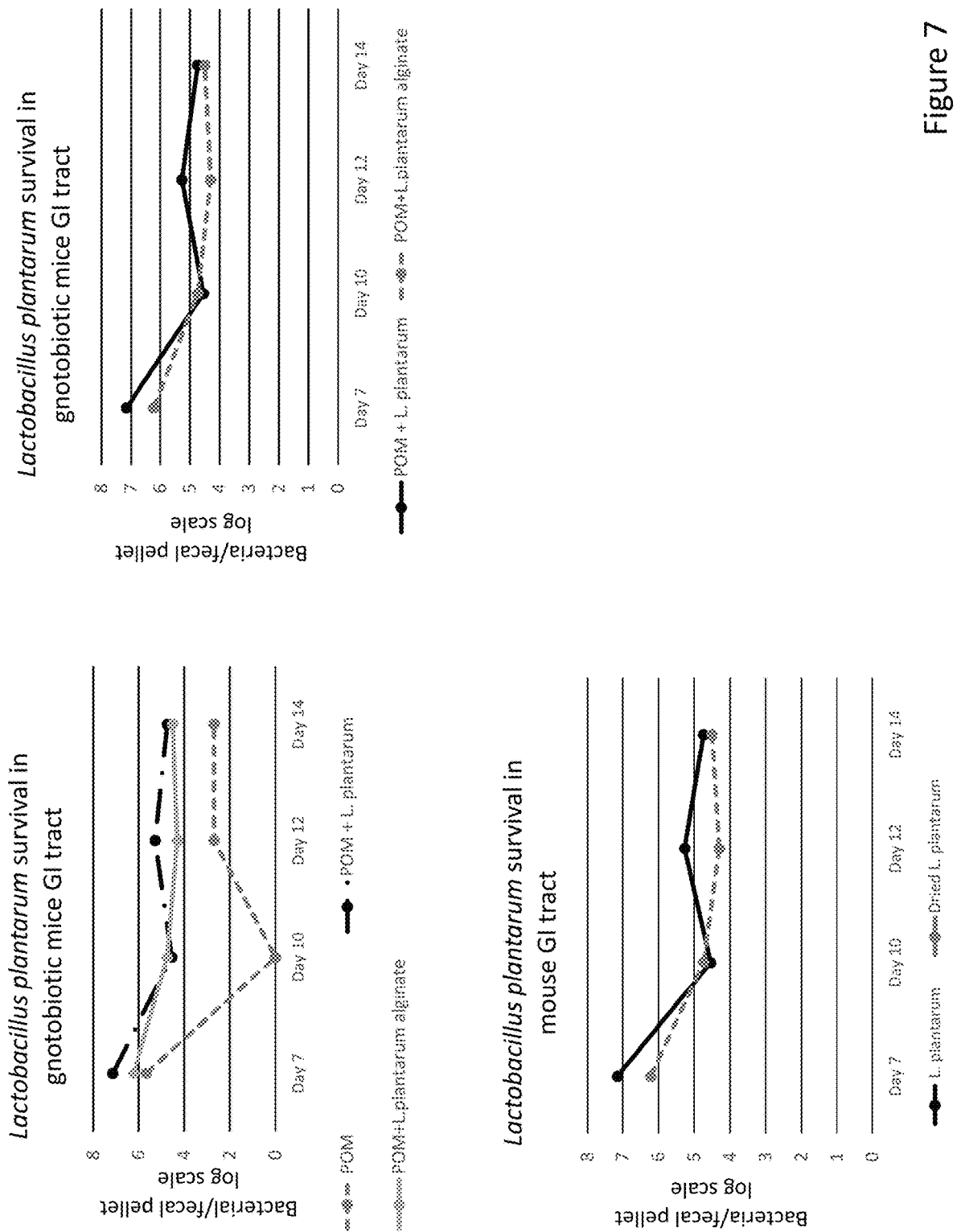
FIG. 7 shows the ability of a biofilm according to some embodiments of the present invention to colonize the gut of an animal model, using the indicated compositions.

FIG. 7 shows that bacteria colonized the gut of the mice. The gut of the mice was colonized with the bacteria derived from the biofilm for more than 3 days, and, in fact, for up to, but not limited to, 14 days.

Figure 8:
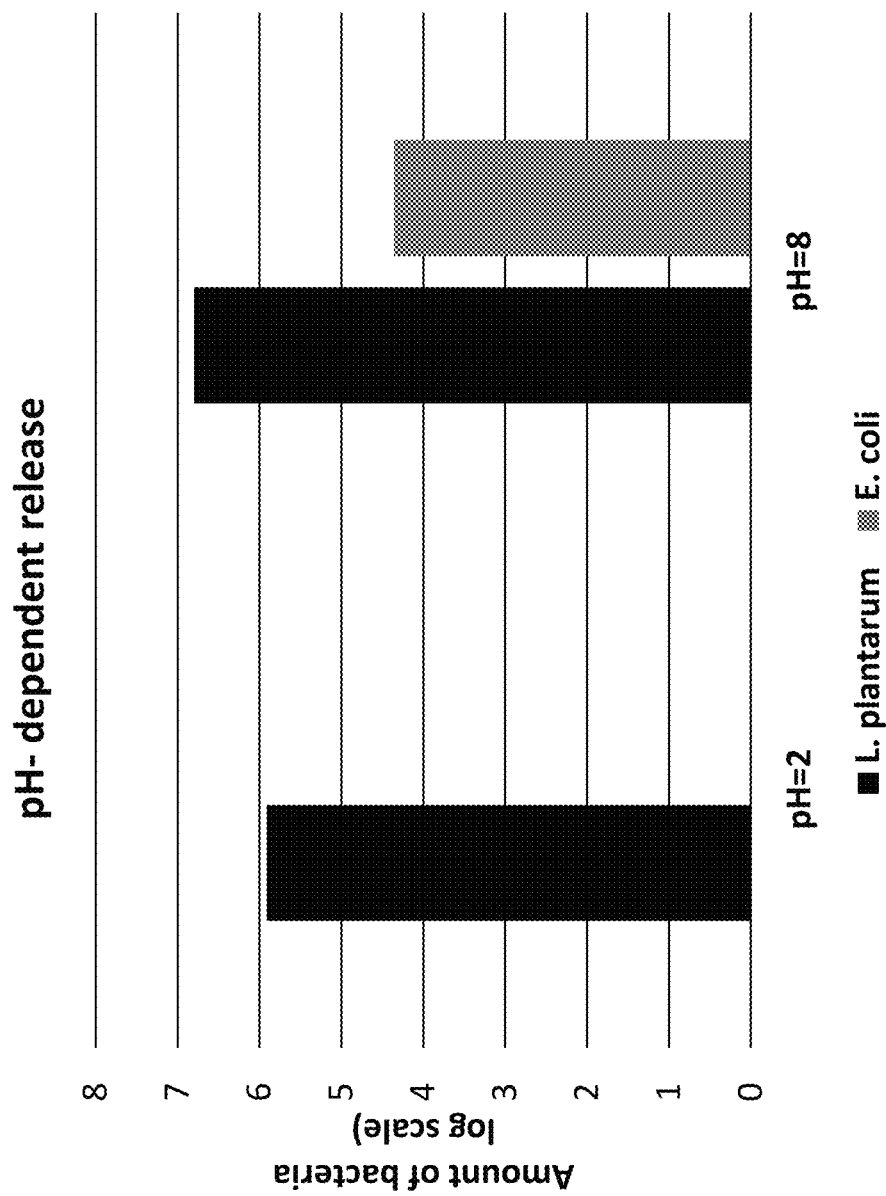
FIG. 8 shows the pH-dependent release of bacteria from biofilms according to some embodiments of the present invention.

Example 6: pH-Dependent Release of Bacteria From a Composition According to Some Embodiments of the Present Invention A biofilm comprising *E. coli* on DCP was encapsulated in alginate by mixing the DCP with the biofilm in 4% alginate and dropping droplets with the material into 2% $CaCl_2$ solution, and a biofilm comprising *L. plantarum* was grown on top of the alginate beads. The resulting compositions were then treated according to Example 1 above. The results are shown in FIG. 8.

Only *Lactobacillus plantarum* was released when the beads were inserted into a solution at pH=2. At pH=8 both *E. coli* and *L. plantarum* were released from the beads.

Example 7: Colonization of Murine Gut Using a Composition Comprising *C. minuta* According to Some Embodiments of the Present Invention A biofilm comprising *C. minuta* on pomegranate seeds was given to SPF mice once at a concentration of 2*$10^7$ bacteria at day 1 of the experiment mixed with the food. Feces were checked at day 1 (before probiotic treatment), 2, 4, 7, 11 and 15 for the % of *C. minuta* in the feces.

The animals were treated as follows (three mice per treatment group):
1. Control—Food only (6 gr).
2. Control—Food (3 gr) mixed with pomegranate grains (3 gr) only
3. Experiment—Food (3 gr) mixed with *C. minuta* biofilm on pomegranate grains (3 gr).

Figure 9:
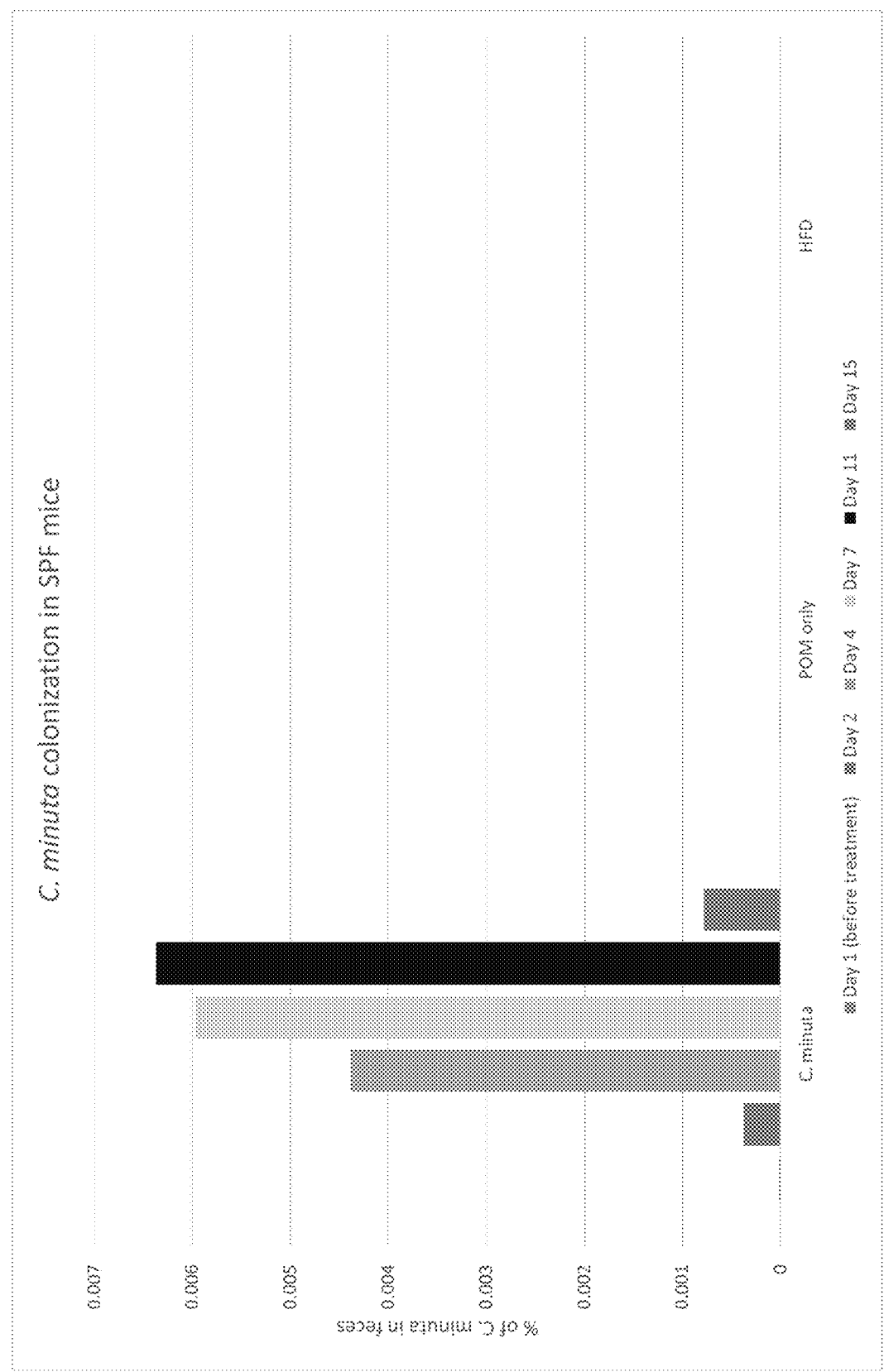
FIG. 9 shows the ability of another biofilm according to some embodiments of the present invention to colonize the gut of an animal model

SPF mice were administered 2*$10^7$ *C. minuta* cells in biofilm on pomegranate grains (*C. minuta*), pomegranate grains (POM only) or just diet (HFD) on the first day of the experiment. Feces samples were taken before the probiotic treatment (Day 1), 2 days, 4 days, 7 days, 11 days and 15 days following the probiotic treatment and sent to 16S sequencing. The percent of *C. minuta* in the overall population of bacteria in each feces sample was calculated. The results are shown in FIG. 9. These data show that the biofilm comprising *C. minuta* was capable of colonizing the gut of mice for up to 15 days, when the experiment was terminated, as evidenced by the presence of *C. minuta* in fecal samples.

Example 8: Colonization of Murine Gut Using a Composition According to Some Embodiments of the Present Invention—Comparison with Other Methods A biofilm comprising *L. plantarum* was grown according to the conditions outline below, and given to SPF mice once at a concentration of $2*10^9$ bacteria per day, for 5 days. After this time, mice were fed with food alone for a further 5 days.

Figure 10:
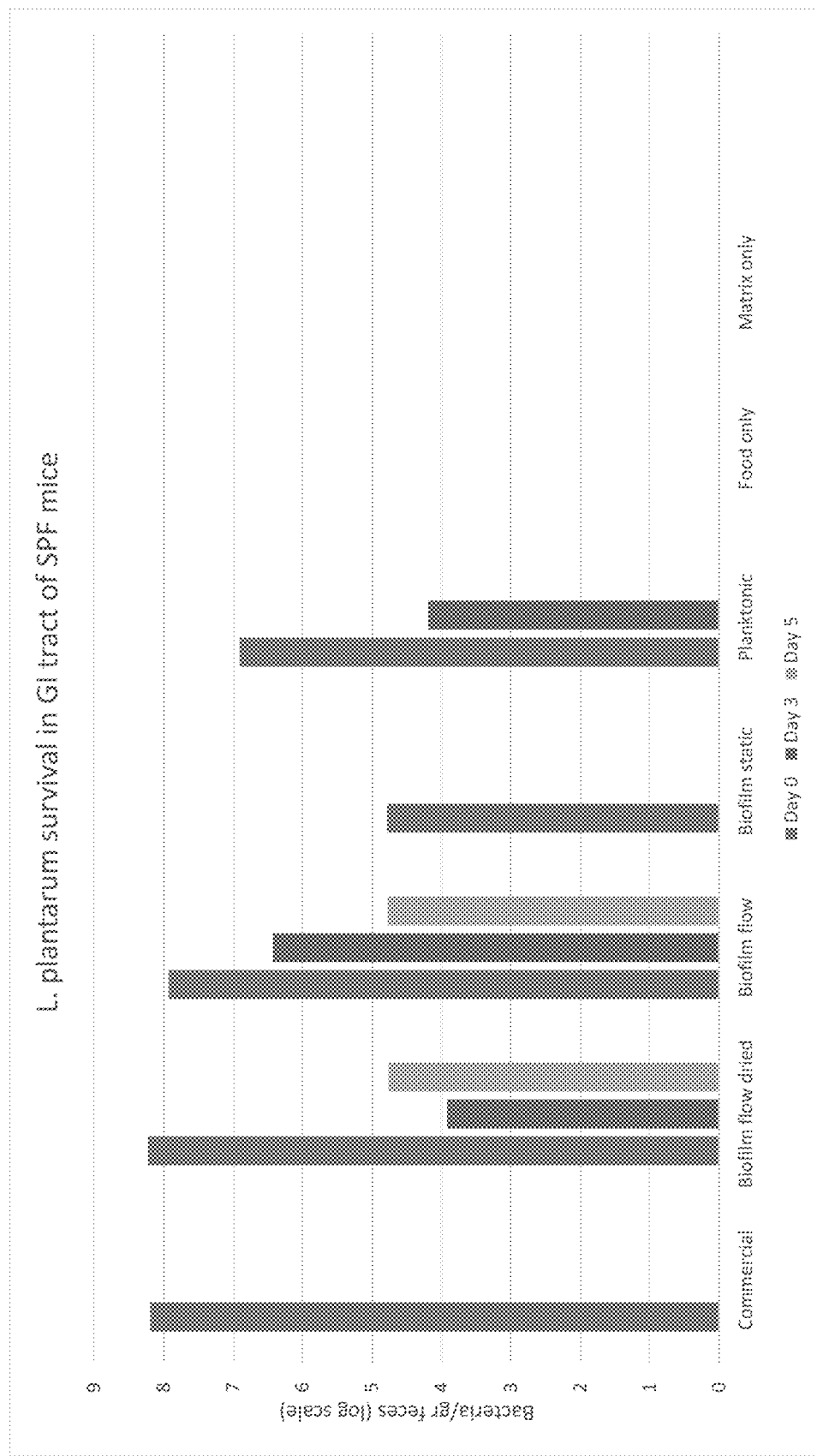
FIG. 10 shows the ability of another biofilm according to some embodiments of the present invention to colonize the gut of an animal model, compared to other biofilms formed using other methods.

The animals were treated as follows (two mice per treatment group):
1. Control—Food only
2. Control—Food with particles (pomegranate grains POM) only.
3. Planktonic. *L. plantarum* was grown overnight in shaking at 37 C in MRS broth.
4. Biofilm static on Pomegranate grains (POM)—5 gr of particles with bacteria (approximately $10^6$ bacteria/day) (according to the methods described in DE202013103204)
5. Biofilm flow on Pomegranate grains (POM)—1.5 gr of particles with bacteria.
6. Biofilm flow on Pomegranate grains (POM) and lyophilized—1.5 gr of particles with bacteria (according to the methods described in Biomacromolecules 2013, 14, 3214-3222).
7. Commercial probiotic supplement—2 pills per day for 5 day The amount of *Lactobacillus* was quantified using colony counts of mice's feces taken at Day 5 (the last day of sample admission), Day 3 and Day 5 (3 and 5 days following cessation of sample admission). The results are shown in FIG. 10. These data show that the biofilm comprising *L. plantarum* formed according to the methods of the present invention was capable of colonizing the gut of mice for up to 5 days, when the experiment was terminated, as evidenced by the presence of *L. plantarum* in fecal samples. However, compositions formed according to the methods described in DE202013103204, or Biomacromolecules 2013, 14, 3214-3222 were not capable of colonizing the gut of mice for up to 5 days.

Publications cited throughout this document are hereby incorporated by reference in their entirety. Although the various aspects of the invention have been illustrated above by reference to examples and preferred embodiments, it will be appreciated that the scope of the invention is defined not by the foregoing description but by the following claims properly construed under principles of patent law.

The invention claimed is:

1. A method for treating a subject in need of a probiotic treatment, the method comprising:
   providing a probiotic composition comprising a bacterial biofilm comprising a population of at least one bacterial strain attached to particles, wherein said particles comprise cellulose and phosphate; and
   administering said probiotic composition to said subject, thereby treating the subject in need of a probiotic treatment.

2. The method of claim 1, wherein each particle comprises a mixture of cellulose and phosphate.

3. The method of claim 1, wherein said cellulose is microcrystalline cellulose (MCC).

4. The method of claim 1, wherein said phosphate is dicalcium phosphate (DCP).

5. The method of claim 1, wherein said particles comprising cellulose and phosphate comprise said cellulose in the form of microcrystalline cellulose (MCC) and said phosphate in the form of dicalcium phosphate (DCP).

6. The method of claim 1, wherein said bacterial biofilm comprising said population of at least one bacterial strain attached to particles is produced in a process comprising a step of culturing the population of at least one bacterial strain with the particles for a time sufficient for the population of at least one strain of bacteria to attach to the particles.

7. The method of claim 1, wherein said bacterial biofilm comprising said population of at least one bacterial strain attached to particles is produced in a process comprising a step of culturing the population of at least one bacterial strain attached to particles under anaerobic conditions.

8. The method of claim 7, wherein said biofilm is produced under said anaerobic conditions.

9. The method of claim 7, wherein the process further comprises the steps of:
   a. inoculation of a population comprising at least one strain of bacteria in a growth medium;
   b. incubation of said particles with said population comprising at least one bacterial strain for a time sufficient for the population of at least one strain of bacteria to attach to said particles; and
   c. culturing of the population comprising said at least one strain of bacteria attached to particles in a growth medium for a time sufficient under anaerobic conditions to form said bacterial biofilm comprising the population of at least one strain of bacteria attached to particles.

10. The method of claim 6, wherein said culturing occurs in a growth medium, and wherein the growth medium exerts a shear force on the bacteria during the culturing step.

11. The method of claim 1, wherein said particles range from 30 to 500 microns in diameter.

12. The method of claim 1, wherein said biofilm is further encapsulated with a compound configured to release the at least one bacterial strain in a pH dependent manner.

13. The method of claim 1, wherein said biofilm is in a lyophilized form.

14. The method of claim 1, wherein said administering results in colonization of the gastrointestinal tract of said subject by the probiotic strain.

15. The method of claim 1, wherein said bacterial biofilm comprising a population of at least one bacterial strain attached to particles is characterized by increased survival and/or colonization in a subject administered therewith.

16. The method of claim 1, wherein said probiotic composition is configured to colonize a gut of said subject for at least five days in a subject administered therewith.

17. The method of claim 1, wherein an amount of $2 \times 10^4$ to $2 \times 10^9$ bacteria per day of said bacterial biofilm comprising a population of at least one bacterial strain is configured to colonize a gut of said subject for 1 to 5 days.

18. The method of claim 1, wherein said at least one bacterial strain is selected from the group consisting of: *Lactobacillus*, *Christensenella*, and *Acetobacter*.

19. The method of claim 1, wherein said bacterial biofilm comprising a population of at least one bacterial strain attached to particles, comprises two or more strains of bacteria attached to said particles.

\* \* \* \* \*